US008148581B2

(12) United States Patent
Pinkos et al.

(10) Patent No.: US 8,148,581 B2
(45) Date of Patent: Apr. 3, 2012

(54) PROCESS FOR PREPARING PLASTICS USING 1,6-HEXANEDIOL HAVING AN ALDEHYDE CONTENT OF LESS THAN 500 PPM

(75) Inventors: Rolf Pinkos, Bad Duerkheim (DE); Eva Kretzschmar, Mannheim (DE); Olivier Abillard, Mannheim (DE); Lionel Gehringer, Schaffhouse-pres-Setlz (FR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/952,861

(22) Filed: Nov. 23, 2010

(65) Prior Publication Data
US 2011/0124905 A1    May 26, 2011

(30) Foreign Application Priority Data
Nov. 26, 2009  (DE) .......................... 10 2009 047 194

(51) Int. Cl.
*C07C 29/74* (2006.01)
*C07C 29/80* (2006.01)
(52) U.S. Cl. ........................................ 568/868; 568/861
(58) Field of Classification Search ............. 568/868, 568/861
See application file for complete search history.

(56) References Cited

FOREIGN PATENT DOCUMENTS

| WO | WO 97/31882 | 9/1997 |
|---|---|---|
| WO | WO 2010/063659 A2 | 6/2010 |
| WO | WO 2010/115738 A1 | 10/2010 |
| WO | WO 2010/115798 A2 | 10/2010 |

OTHER PUBLICATIONS

U.S. Appl. No. 12/953,004, filed Nov. 23, 2010, Pinkos, et al.
U.S. Appl. No. 12/952,956, filed Nov. 23, 2010, Pinkos.
Klaus Weissermel et al., "Industrielle Organische Chemie", 5$^{th}$ complete revised edition, Wiley-VCH, 5 pages.
Klaus Weissermel et al., "Industrielle Organische Chemie", 5$^{th}$ complete revised edition, Wiley-VCH, 5 pages, 1978.
U.S. Appl. No. 13/133,006, filed Jun. 6, 2011, Abillard, et al.
U.S. Appl. No. 13/258,166, filed Sep. 21, 2011, Pinkos, et al.
U.S. Appl. No. 13/257,496, filed Sep. 19, 2011, Pinkos, et al.
U.S. Appl. No. 13/226,049, filed Sep. 6, 2011, Abillard, et al.

*Primary Examiner* — Elvis O Price
(74) *Attorney, Agent, or Firm* — Oblon, Spivak, McClelland, Maier & Neustadt, L.L.P.

(57) ABSTRACT

The present invention relates to a process for preparing plastics using 1,6-hexanediol having an aldehyde content of less than 500 ppm, a process for preparing 1,6-hexanediol having an aldehyde content of less than 500 ppm and also 1,6-hexanediol having an aldehyde content of less than 500 ppm.

13 Claims, No Drawings

PROCESS FOR PREPARING PLASTICS USING 1,6-HEXANEDIOL HAVING AN ALDEHYDE CONTENT OF LESS THAN 500 PPM

The present invention relates to a process for preparing plastics using 1,6-hexanediol having an aldehyde content of less than 500 ppm, a process for preparing 1,6-hexanediol having an aldehyde content of less than 500 ppm and also 1,6-hexanediol having an aldehyde content of less than 500 ppm.

1,6-Hexanediol is a valuable intermediate for the preparation of polyesters, acrylates or polyurethanes. 1,6-Hexanediol is generally obtainable by hydrogenation of adipic acid or adipic acid-comprising feed streams comprising adipic acid, for example in water or as ester such as dimethyl adipate, or by hydrogenation of hydroxycaproic acid or esters thereof or by hydrogenation of caprolactone, as described by K. Weissermel, H.-J. Arpe et al. in Industrielle Organische Industrie, fifth edition, Wiley-VCH, pages 267 and 269.

Commercially available 1,6-hexanediol still has, despite a high purity of 99.8% by area, components which can restrict its range of uses, as indicated, for example, in the data sheet of Lanxess. 1,6-Hexanediol is described as a white to slightly yellowish solid or a similar liquid comprising up to 0.1% by weight of 6-hydroxyhexanal. It is generally known that the presence of aldehydes limits the color number stability of products. These aldehydes can be present in free form but also as hemiacetals or acetals and as such likewise have an adverse effect on the color number of products, for example polyesters. In addition, such compounds are also undesirable in terms of uses since they are not diols and, for example in the preparation of polyesters, lead to chain termination or to branches.

Polyesters and in particular polyester alcohols are usually prepared by polycondensation reactions of polybasic carboxylic acids/carboxylic acid derivatives with polyhydric alcohols or polyols at temperatures of, in particular, 150-280° C. under atmospheric pressure and/or a slightly reduced pressure in the presence of catalysts. In the present case, the following components based on 6-hydroxyhexanal or 6-hydroxyhexanal itself are relevant as undesirable impurities and are subsumed under the generic term "aldehyde" for the purposes of the present invention:

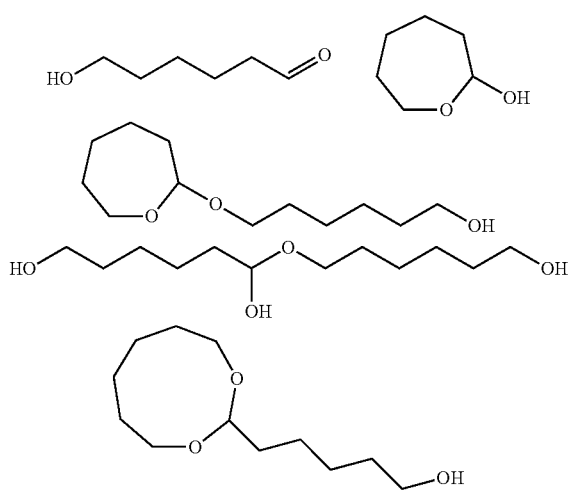

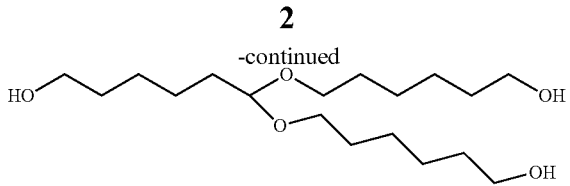

A further component which can be formed from hydroxyhexanal and is likewise undesirable in relatively large amounts is the 1,6-hexanediolester of 6-hydroxycaproic acid, shown below:

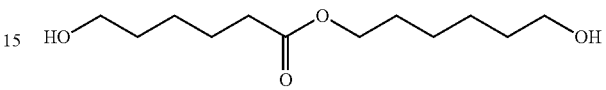

This ester can be formed from 1,6-hexanediol under the same undesirable conditions as 6-hydroxyhexanal. This ester can be measured by means of a base number and is determined by titration with KOH. If the base number is, for example, 8 and is due solely to the abovementioned ester, the ester content is about 33 ppm. The ester can in principle be measured as diol and at contents below 500 ppm, in particular below 50 ppm, generally does not interfere in polyester applications and also does not impart a color.

It is therefore an object of the present patent application to provide a process for preparing plastics, which makes it possible to prepare these with color numbers of less than 150 APHA-Hazen in accordance with ISO 6271. A further object of the present invention is to provide a process by means of which 1,6-hexanediol which itself has a color number of less than 30 APHA-Hazen and at the same time has a purity of greater than 97% with an aldehyde content of less than 500 ppm can be prepared.

This object is achieved by a process for preparing a plastic, which comprises reacting 1,6-hexanediol with dicarboxylic acids or diisocyanates in the presence of at least one catalyst, where the 1,6-hexanediol is a 1,6-hexanediol which has, after its preparation by hydrogenation, been subjected to at least one distillation in which the molar ratio of oxygen to 1,6-hexanediol is less than 1:100 and ≦5 ppm of catalytically active components are present during the distillation and has an aldehyde content of less than 500 ppm.

The invention further provides a process for preparing 1,6-hexanediol having an aldehyde content of <500 ppm, which comprises the following steps:

I) provision of a mixture comprising 1,6-hexanediol,
II) if appropriate, removal of catalytically active components to a residual content of ≦5 ppm,
III) distillation of the mixture obtained from step I or II, where the molar ratio of oxygen to 1,6-hexanediol during the distillation is less than 1:100 and the content of catalytically active components is ≦5 ppm,
IV) collection of the 1,6-hexanediol having an aldehyde content of less than 500 ppm obtained from step III.

The invention further provides 1,6-hexanediol having an aldehyde content of less than 500 ppm which can be obtained by the process of the invention.

For the process of the invention for preparing plastics, it is necessary to use 1,6-hexanediol which is distilled beforehand with substantial exclusion of oxygen and comprises less than 5 ppm of catalytically active, in particular dehydrogenatively active, component during the distillation. The purity of the products obtained and the figures for the aldehyde contents and the amounts of catalytically active components have been determined by gas chromatography and are in the present patent application reported as percentages by area or should be taken as such.

The mixture provided in step I of the process of the invention preferably comprises the 1,6-hexanediol to be isolated in amounts of ≧10% by weight, particularly preferably ≧30% by weight, based on the mixture of step I.

During the distillation of the 1,6-hexanediol in step III of the process of the invention, the molar ratio of oxygen to 1,6-hexanediol should not exceed a ratio of 1:100. Preference is given to a ratio of less than 1:1000, particularly preferably less than 1:10 000. The distillation can be carried out in one or more distillation units. Preference is given to one distillation unit. Suitable columns for the distillation are all columns known to those skilled in the art. Preference is given to packed columns, tray columns with sieve trays, columns with dual-flow trays, columns with bubble cap trays or rectification columns equipped with valve trays, dividing wall columns or thin film evaporators and falling film evaporators, which are preferably operated under reduced pressure. Preference is given to using at least one distillation unit. This is generally at least one column selected from the group consisting of packed columns, tray columns with sieve trays, columns with dual-flow trays, columns with bubble cap trays or rectification columns equipped with valve trays, divided wall columns or thin film evaporators and falling film evaporators, which are preferably operated under reduced pressure at elevated temperatures. The molar ratio of oxygen to 1,6-hexanediol is less than 1:100, preferably less than 1:1000, particularly preferably less than 1:10 000. If desired, a single-stage or multi-stage vaporization of the mixture comprising 1,6-hexanediol and obtained from step I or II can also be carried out before step III of the process of the invention.

The lower the distillation pressure, the more attention has to be paid to the freedom from leaks of the distillation apparatuses used. This increased freedom from leaks can in the case of columns be achieved by means of specific seals selected from the group consisting of welded lip seals, seals having comb profiles and by use of particularly smooth sealing surfaces and by avoidance of a plurality of flanges or access points in the columns, for example for the measurement of pressure, temperature or sight glasses.

A further possibility for avoiding oxygen is to provide the distillation units with an outer jacket which is, for example, made inert by means of nitrogen or argon.

A further measure for reducing the oxygen content during the distillation is welding flanges closed.

One possible way of being able to determine the oxygen content during the distillation is to collect the offgas from the vacuum unit and analyze the gas mixture obtained to determine its composition. The best way of obtaining information on the introduction of oxygen into the column is to operate the column under the preferred conditions but without feed.

Catalytically active and in particular dehydrogenatively active components are firstly catalytically active surfaces within the column, for example at vaporizers, column bodies or internals, rust or other points of corrosion, and secondly catalytically active residues from the preparation of 1,6-hexanediol due to, for example, catalyst residues from the preceding hydrogenation of a carbonyl compound to form 1,6-hexanediol. Preferred catalytically active and in particular dehydrogenatively active components are selected from the group consisting of Cu, Co, Ni, Pd, Fe and Ru, metallic, as alloys, oxides and/or halides and/or carboxylates such adipates and/or 6-hydroxycaproate and mixtures comprising the pure metals, alloys, oxides and/or halides of Cu, Co, Ni, Pd, Fe and Ru. Calculated as metal, both as individual component and as a mixture, the content of catalytically active components in the feed stream to the 1,6-hexanediol column and in particular to the 1,6-hexanediol column should be ≦5 ppm, preferably ≦3 ppm, particularly preferably ≦1 ppm. Preference is given to discharging a corresponding amount of metal and/or mixture of metals from the column together with the bottom stream in order to avoid accumulation in the 1,6-hexanediol column, so that when an amount of, for example, 1 g/hour of metal is present in the feed, 1 g/hour of metal is also discharged in the bottom stream from the column.

To keep the influence of traces of metal in the feed to the 1,6-hexanediol column very small, preference is given to having the feed point, where possible, at a low height of the column, i.e. below the middle of the column, particularly preferably below the lower third of the column, so that the traces of metal have a very short residence time in the column. This also applies to the case of oxygen intruding into the column. Ideally, the feed is introduced into the bottom or bottom circuit of the column. However, the separation task can require the feed point to be positioned at a higher level, e.g. in the middle third of the column. This ultimately determines the degree of other components such as high boilers, e.g. ethers and esters, which have a boiling point higher than that of 1,6-hexanediol in the 1,6-hexanediol to be distilled. In contrast, there are the ethers and esters which have a boiling point lower than that of 1,6-hexanediol and belong to the class of low boilers selected from the group of pentanediols such as 1,5-pentane-diol or hexanediols such as 1,2- and/or 1,4-cyclohexanediols or 1,5-hexanediol.

The greater the amount of high-boiling secondary components whose boiling point under the given distillation conditions is more than 50° C. higher than that of the actual 1,6-hexanediol is comprised, the higher does the feed point have to be installed on the column. If a dividing wall column is used, the feed point is always at the height of the dividing wall, preferably at the height of the middle third of the dividing wall. The same applies to the side offtake which is likewise located at the height of the middle third of the dividing wall, preferably opposite the feed point. However, this side offtake does not have to be located precisely opposite the feed point but can also be located above or below this point within the middle third of the dividing wall.

Catalytically active components also include catalytically active surfaces which can, for example, be avoided by manufacturing the entire column with internals made of stainless steel or ensuring that all points of corrosion present are carefully removed before operation of the column. To avoid points of corrosion which continue to occur, the acid number (mg of KOH/100 g of sample), for example, in the feed to the distillation should be less than 10, preferably less than 5, particularly preferably less than 1.

Further catalytically active components are catalyst residues which are comprised, for example, in the preparation of the 1,6-hexanediol used in the process of the invention. In particular, the preparation of 1,6-hexanediol is carried out in the presence of hydrogenation catalysts whose catalyst residues can also be comprised in the end product obtained. Although the development of chemically and mechanically stable catalysts has made great progress, these catalysts cannot avoid catalyst discharge residues being entrained in the 1,6-hexanediol during start-up or shutdown or during flushing of the parts of the plant in which the catalyst is comprised. It is therefore advantageous for the 1,6-hexanediol used in the process of the invention to be freed of catalyst discharge residues before the distillation so that these are not introduced at all into the distillation column. Catalyst constituents can be entrained heterogeneously or else homogeneously in the product stream from the preparation of the 1,6-hexanediol. One possible measure for reducing the heterogeneous catalyst constituents is a filter upstream of the distillation of the 1,6-hexanediol in step III of the process of the invention. Particular preference is given to using the filter directly after the hydrogenation. The filters are selected from the group consisting of candle filters, membrane filters and filter aids such as activated carbon and kieselguhr. The candle and membrane filters have a mesh opening which is smaller than the catalyst discharge particles and is preferably below 0.1 mm, particularly preferably less than 0.05 mm. The candle and membrane filters can be made of metal or ceramic, and the metal of the filter must not have any catalytically active surface for the subsequent distillation of the 1,6-hexanediol. Such filter units used can be configured as a crossflow filtration or in the case of filter aids as a deep bed filtration in which a filtercake ensures that no or only a very small amount of heterogeneous catalyst constituents get into the distillation. If desired, the fixed filter units can also be combined with the filter aids when they are carried out in succession. Homogeneously dissolved catalyst constituents can be removed by means of chemically induced precipitation or by means of ion exchangers. Preference is given to using ion exchangers. For the process of the invention, it is advantageous for the 1,6-hexanediol to be distilled to have a content of catalytically active components of ≦5 ppm before introduction into the distillation.

It is advantageous for the catalytically active components, e.g. catalyst discharge constituents, to be removed early in the process for preparing the 1,6-hexanediol according to the invention. This can be achieved either by carrying out step II of the process of the invention before or after a single-stage or multistage vaporization of the mixture comprising 1,6-hexanediol from step I of the process of the invention. Preference is given to removing the catalytically active components before the single-stage or multistage vaporization. The use of a single-stage or multistage vaporization is advantageous when the 1,6-hexanediol having an aldehyde content of less than 500 ppm is to be prepared by a continuous process. When carrying out the single-stage or multistage vaporization, it is advantageous for the vaporization to be carried out at pressures below 200 mbar, preferably below 100 mbar, and temperatures below 230° C., advantageously below 180° C., and residence times of less than 60 min, preferably less than 40 min, since otherwise undesirable dehydrogenation reactions can occur during this vaporization step.

A 1,6-hexanediol which has been pretreated in this way can subsequently be distilled in a distillation column as per step III of the process of the invention at an oxygen/diol ratio of less than 1:100, so that the 1,6-hexanediol has an aldehyde content of less than 500 ppm.

Should, in the preparation of 1,6-hexanediol, catalytically active components have got into the distillation column of step III of the process in sufficient amounts for the aldehyde content to have become greater than 500 ppm despite the use of appropriate filters, the column should be cleaned. This can be effected by intensive flushing with, for example, water and/or acids, preferably by flushing with $HNO_3$. Traces of, for example, Cu and/or Co can also be removed by flushing with $HNO_3$. Preference is given to an $HNO_3$ concentration in water of 1-20% by weight.

If it is not possible to undertake measures for avoiding oxygen and/or catalytically active components or should these measures be insufficient, it is in principle also possible to carry out the distillation of 1,6-hexanediol at very low pressures since in this way the distillation temperatures are reduced and chemical reactions such as oxidation and/or dehydrogenations proceed more slowly. However, this has the disadvantage that the lower the pressure, the greater the outlay for vacuum equipment and columns. For example, at a very low pressure the mass throughput through the column decreases so that the latter has to be made with a larger diameter, which incurs considerable additional costs. A process which makes it possible to work at an oxygen/1,6-hexanediol ratio of less than 1:100 and/or to avoid catalytic dehydrogenations is therefore more advantageous. The preferred distillation pressure in step III of the process of the invention is therefore above 25 mbar, preferably above 40 mbar, particularly preferably above 75 mbar. The upper limit is 500 mbar, preferably 300 mbar.

The present invention therefore not only provides for the use of a 1,6-hexanediol prepared in this way for preparing polyesters, polyurethanes and acrylates but also provides the process for preparing 1,6-hexanediol which has an aldehyde content of less than 500 ppm, preferably less than 400 ppm, very particularly preferably less than 100 ppm and most particularly preferably less than 50 ppm. The invention therefore further provides a 1,6-hexanediol prepared by this process which has an aldehyde content of less than 500 ppm. A 1,6-hexanediol prepared in this way not only has the low proportion of aldehyde but also a color number determined in accordance with ISO 6271 of less than 30 APHA-Hazen. Such a 1,6-hexanediol thus leads in the reaction with, for example, carboxylic acids in the presence of catalysts to polyesters which have a color number (Hazen color number) determined in accordance with ISO 6271 of less than 150 APHA-Hazen, preferably less than 120 APHA-Hazen, very particularly preferably less than 100 APHA-Hazen.

To prepare the polyesters, the 1,6-hexanediol prepared in this way is reacted with carboxylic acids selected from the group consisting of succinic acid, maleic acid, fumaric acid, glutaric acid, adipic acid, dodecanedioic acid, terephthalic acid, isophthalic acid and phthalic acid, particularly preferably succinic acid and adipic acid. For the preparation of polyurethanes, the 1,6-hexanediol is reacted with isocyanates selected from the group consisting of hexamethylene diisocyanate, tolylene 2,4-diisocyanate, diphenylmethane diisocyanate, isophorone diisocyanate and 4,4'-diisocyanatodicyclohexylmethane. To produce both the polyesters and the polyurethanes, further catalysts can be used. These are selected from the group consisting of acids, bases, Lewis acids and Lewis bases.

EXAMPLES

The determination of the aldehyde content is carried out by gas chromatography. For this purpose, a column DB5 having a length of 60 m, an internal diameter of 0.32 mm and a film thickness of 1 μm is used. For the measurement, a temperature profile in which a temperature of 90° C. is held isothermally at the beginning for 5 minutes, a heating rate of 5° C./minute is subsequently set until 150° C. have been reached, a heating rate of 1° C./minute is then set up to 160° C., then a heating rate of 5° C./minute is set to 200° C. and subsequently a heating rate of 20° C./minute is set to 300° C., followed by a 20 minute isothermal phase is employed. The injector temperature was 250° C., while the FID temperature was 320° C. The figures reported for the aldehyde content of the 1,6-hexanediol are determined as GC-% by area, preferably when the content of 1,6-hexanediol is >97% and the content of aldehyde is <1000 ppm.

The following examples illustrate how a 1,6-hexanediol having an aldehyde content of below 500 ppm is obtained and also what effect an increased aldehyde content has.

Comparative Example 1

Preparation of Hexanediol

Dimethyl adipate is hydrogenated in the gas phase at 60 bar and 195-210° C. over a copper-comprising catalyst. The collected outputs (about 36% of methanol, about 67% of 1,6-hexanediol, remainder predominantly 6-hydroxycaproic esters, hexanol and further compounds present in an amount of less than 500 ppm, including 6-hydroxyhexanal, and about 15 ppm of Cu (presumably due to entrainment of dust) are worked up by distillation. Here, predominantly methanol is firstly removed at temperatures at the bottom up to 110° C. and pressures of from 1013 mbar absolute to 500 mbar. The remaining bottoms are fractionally distilled batchwise in a distillation column (1 m packed column, reflux ratio 5, no access of air) at 50 mbar absolute and temperatures at the bottom of about 180° C. After removal of low boilers such as residual methanol and hexanol, 1,6-hexanediol is obtained in a distillation yield of about 90% and a purity of 99.9%. The 6-hydroxyhexanal content was 500 ppm.

Preparation of Polyester:

1325.3 g of adipic acid, 396.6 g of 1,6-hexanediol having a 6-hydroxyhexanal content of 500 ppm, 623.0 g of 1,4-butanediol and 10 ppm of tin octoate were placed in a round-bottom flask having a volume of 4 liters. The mixture was heated to 180° C. while stirring and maintained at this temperature for 3 hours. The water formed was removed by distillation during this process.

The mixture was then heated to 240° C. and maintained at this temperature under a reduced pressure of 40 mbar until an acid number below 1 mg KOH/g had been reached.

The liquid polyester alcohol formed had the following properties:

| | |
|---|---|
| Hydroxyl number: | 54.1 mg KOH/g |
| Acid number: | 0.1 mg KOH/g |
| Viscosity: | 690 mPa · s at 75° C. |
| Water content: | 0.01% |
| Color number: | 210 APHA-Hazen |

Example 1

Preparation of Hexanediol

Comparative example 1 is repeated with the difference that the product stream is, after methanol has been separated off, freed of high-boiling components by means of a thin film evaporator (Sambay) at 50 mbar. The 1,6-hexanediol obtained after this distillation had a purity of over 99.9%, and the 6-hydroxyhexanal content was below 50 ppm.

Preparation of Polyester:

1325.3 g of adipic acid, 396.6 g of 1,6-hexanediol having a 6-hydroxyhexanal content of less than 50 ppm, 623.0 g of 1,4-butanediol and 10 ppm of tin octoate were placed in a round-bottom flask having a volume of 4 liters. This mixture was heated to 180° C. while stirring and maintained at this temperature for 3 hours. The water formed was removed by distillation during this process.

The mixture was then heated to 240° C. and maintained at this temperature under a reduced pressure of 40 mbar until an acid number below 1 mg KOH/g had been reached.

The liquid polyester alcohol formed had the following properties:

| | |
|---|---|
| Hydroxyl number: | 56.8 mg KOH/g |
| Acid number: | 0.2 mg KOH/g |
| Viscosity: | 530 mPa · s at 75° C. |
| Water content: | 0.01% |
| Color number: | 68 APHA-Hazen |

Comparative example 2

A mixture of dimethyl adipate, methyl 6-hydroxycaproate prepared in a manner analogous to that described in WO97/31882, Example 1 (variant A) is hydrogenated as indicated. Immediately after start-up, a mixture comprising methanol and 1,6-hexanediol and also traces of catalyst but according to GC analysis no 6-hydroxyhexanal is obtained. Methanol was distilled off from this mixture. The resulting crude hexanediol comprised about 150 ppm of the Cu catalyst as impurity. 135 g of this mixture were fractionally distilled in a column at 150 mbar and temperatures at the bottom of about 195° C. without air getting into the distillation system. This gave a fraction which comprised the major part of the 1,6-hexanediol but in which not only 93.7% of 1,6-hexanediol but also 5.6% of 6-hydroxyhexanal were present. In addition, 0.2% of 1,5-pentanediol and also a plurality of components each in amounts of less than 1000 ppm, including about 500 ppm of 1,4-cyclohexanediol, were present.

After operation of the hydrogenation for 2 days, 16 ppm of Cu catalyst were still present in the crude hexanediol. In the subsequent distillation of crude hexanediol, the fraction containing the most hexanediol comprised 99.25% of 1,6-hexanediol together with 2100 ppm of 6-hydroxyhexanal.

Example 2

Comparative example 2 was repeated, with the hydrogenation output being filtered through a filter (5 μm mesh opening). Only 2 ppm of Cu catalyst were found in the crude hexanediol. In the subsequent distillation of crude hexanediol, the fraction comprising the most hexanediol comprised 99.64% of 1,6-hexanediol together with only 450 ppm of 6-hydroxyhexanal.

Example 3

Example 2 was repeated, but no Cu catalyst could be detected (detection limit 2 ppm) in the crude hexanediol because the hydrogenation output had been filtered through a filter (0.5 μm mesh opening). In the subsequent distillation of the crude hexanediol, the fraction comprising the most hexanediol comprised 99.7% of 1,6-hexanediol together with only 40 ppm of 6-hydroxyhexanal.

Comparative Example 3

Example 1 was repeated except that some leakage air got into the system during the hexanediol distillation (molar ratio of oxygen to hexanediol about 1:90). The fraction comprising the most hexanediol comprised 99.3% of 1,6-hexanediol together with 3000 ppm of 6-hydroxyhexanal.

When the molar ratio of oxygen to hexanediol was reduced to 1:1000 under otherwise identical conditions, the 6-hydroxyhexanal content was only 350 ppm.

The invention claimed is:

1. A process for preparing a plastic, which comprises reacting 1,6-hexanediol with at least one dicarboxylic acid or at least one diisocyanate in the presence of at least one catalyst, where the 1,6-hexanediol is a 1,6-hexanediol which has, after its preparation by hydrogenation, been subjected to at least one distillation in which the molar ratio of oxygen to 1,6-hexanediol is less than 1:100 and ≦5 ppm of catalytically active components are present during the distillation, the 1,6-hexanediol having an aldehyde content of less than 500 ppm.

2. The process according to claim 1, wherein the plastic is selected from the group consisting of polyesters, polyurethanes and polyacrylates.

3. The process according to either claim 1 or 2, wherein a single-stage or multistage vaporization at pressures of ≦200 mbar and temperatures of ≦230° C. is carried out before the distillation.

4. The process according to either claim 1 or 2, wherein the 1,6-hexanediol is freed of catalytically active components before the distillation.

5. The process according to claim 4, wherein the catalytically active components are selected from the group consisting of metallic Cu, Co, Ni, Pd, Fe and Ru, alloys thereof and compounds thereof with oxides and/or halides and/or carboxylates and mixtures of these components.

6. The process according to claim 4, wherein the catalytically active components are removed by filtration, precipitation and/or ion exchange.

7. The process according to claim 6, wherein the catalytically active components are removed by mechanical filters having a mesh opening of <0.1 mm.

8. A process for preparing 1,6-hexanediol having an aldehyde content of <500 ppm, which comprises:
  distillation of a mixture comprising 1,6-hexanediol, said mixture comprising ≦5 ppm catalytically active components, where the ratio of oxygen to 1,6-hexanediol during the distillation is less than 1:100
  to provide 1,6-hexanediol having an aldehyde content of less than 500 ppm.

9. The process according to claim 8, further comprising a single-stage or multistage vaporization of said mixture comprising 1,6-hexanediol at pressures of ≦200 mbar and temperatures of ≦230° C. prior to said distillation.

10. The process according to claim 8, wherein the catalytically active components are selected from the group consisting of metallic Cu, Co, Ni, Pd, Fe and Ru, alloys thereof and compounds thereof with oxides and/or halides and/or carboxylates and mixtures of these components.

11. A 1,6-hexanediol having an aldehyde content of less than 500 ppm obtained by the process according to claim 8, 9 or 10.

12. The process according to claim 3, wherein the 1,6-hexanediol is freed of catalytically active components before the distillation.

13. The process according to claim 12, wherein the catalytically active components are selected from the group consisting of metallic Cu, Co, Ni, Pd, Fe and Ru, alloys thereof and compounds thereof with oxides and/or halides and/or carboxylates and mixtures of these components.

* * * * *